United States Patent [19]

Childress

[11] 4,006,250
[45] Feb. 1, 1977

[54] SYSTEMIC TREATMENT OF PSORIASIS

[75] Inventor: Scott J. Childress, Philadelphia, Pa.

[73] Assignee: American Home Products Corporation, New York, N.Y.

[22] Filed: Aug. 25, 1975

[21] Appl. No.: 607,647

[52] U.S. Cl. .............................................. 424/326
[51] Int. Cl.² ..................................... A61K 31/155
[58] Field of Search ................................... 424/326

[56] References Cited

UNITED STATES PATENTS 3,591,636  7/1971  Houlihan et al. ................... 424/326

Primary Examiner—Norman A. Drezin
Attorney, Agent, or Firm—Stephen I. Miller; Robert Wiser

[57] ABSTRACT

A process for the treatment of psoriasis by systemic administration of 1-(2,6-dihalobenzylideneamino)-3-hydroxyguanidines is disclosed.

12 Claims, No Drawings

SYSTEMIC TREATMENT OF PSORIASIS

BACKGROUND OF THE INVENTION

Psoriasis is a disease of the skin, whose etiology is unknown. The skin lesions associated with psoriasis may be described as dull red patches or plaques of scaly erythema. The scales are distinctive, having a slightly opalescent silvery appearance. The disease has a predilection for certain areas of the body; thus the scalp, the extensor surfaces of the extremeties (particularly at the elbows and knees), the back and the buttocks are most usually affected. However, the nails, eyebrows, axillae, umbilicus and anogenital regions are also frequent sites of involvement.

To date, there has been no report of a complete and permanent cure for psoriasis, and although the several treatments of choice available afford temporary remission of the symptoms, recurrence is almost certain. Most treatments involve the topical application of steroid (e.g. the adrenocortical steroids) ointments and creams, and no clinically successful, long-term, systemic treatment for the disease is currently available.

The compounds utilized in the process of the invention, substituted benzylideneamino-3-hydroxyguanidines and their pharmacologically acceptable acid addition salts, have previously been described in the literature. For example, U.S. Pat. No. 3,591,636 described the preparation of this class of compounds and discloses their utility as hypotensive agents and agrochemicals (i.e. antifungals and herbicides). In addition the preparation of the substituted benzaldehydes from which the benzylideneamino-3-hydroxyguanidines of the invention may be prepared is described in Chemical Abstracts, 26, 1271 (1931); 31, 3816 (1936).

SUMMARY OF THE INVENTION

The invention sought to be patented in a principal process aspect resides in the concept of a process for treating a human being suffering from psoriasis which comprises administration of an effective amount of a compound of the formula:

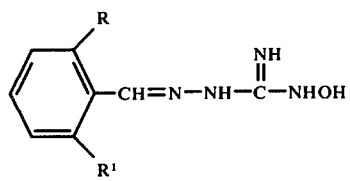

wherein R and R[1] are independently chlorine and fluorine, and the pharmacologically acceptable acid addition salts thereof.

The invention sought to be patented in its first subgeneric process aspect resides in the concept of a process for treating a human being suffering from psoriasis which comprises administration of an effective amount of the compound of the formula:

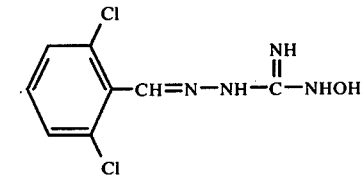

and the pharmacologically acceptable acid addition salts thereof.

The invention sought to be patented in its second subgeneric process aspect resides in the concept of a process for treating a human being suffering from psoriasis which comprises administration of an effective amount of the pharmacologically acceptable salt of the formula:

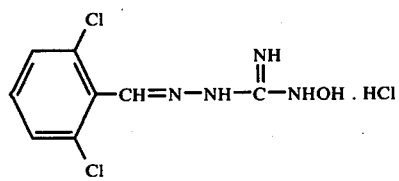

The invention sought to be patented in its third subgeneric process aspect resides in the concept of a process for ameliorating the clinical manifestations of psoriasis in a human being suffering from psoriasis which comprises administration of an effective amount of a compound of the formula:

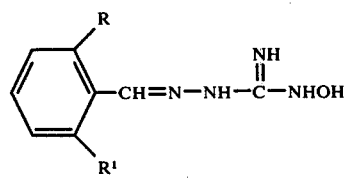

wherein R and R[1] are independently chlorine and fluorine, and the pharmacologically acceptable acid addition salts thereof.

The invention sought to be patented in its fourth subgeneric process aspect resides in the concept of a process for ameliorating the clinical manifestations of psoriasis in a human being suffering from psoriasis which comprises administration of an effective amount of the compound of the formula:

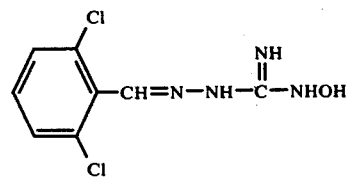

and the pharmacologically acceptable acid addition salts thereof.

The invention sought to be patented in its fifth subgeneric process aspect resides in the concept of a process for ameliorating the clinical manifestations of psoriasis in a human being suffering from psoriasis which comprises administration of an effective amount of pharmacologically acceptable salt of the formula:

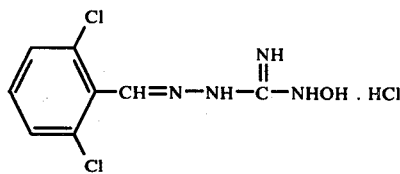

The invention sought to be patented in its sixth subgeneric aspect resides in the concept of a process for decreasing the psoriatic scaling experienced by a human being suffering from psoriasis which comprises administration of an effective amount of a compound of the formula:

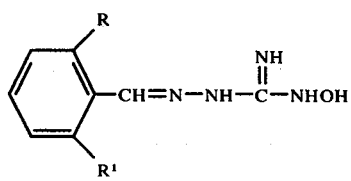

wherein R and $R^1$ are independently chlorine and fluorine, and the pharmacologically acceptable acid addition salts thereof.

The invention sought to be patented in its seventh subgeneric process aspect resides in the concept of a process for decreasing the psoriatic scaling experienced by a human being suffering from psoriasis which comprises administration of an effective amount of the compound of the formula:

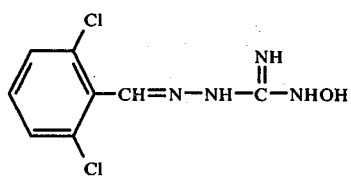

and the pharmacologically acceptable acid addition salts thereof.

The invention sought to be patented in its eighth subgeneric process aspect resides in the concept of a process for decreasing the psoriatic scaling experienced by a human being suffering from psoriasis which comprises administration of an effective amount of the pharmacologically acceptable salt of the formula:

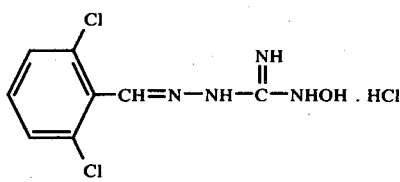

The invention sought to be patented in its ninth subgeneric aspect resides in the concept of a process for decreasing the psoriatic erythema experienced by a human being suffering from psoriasis which comprises administration of an effective amount of a compound of the formula:

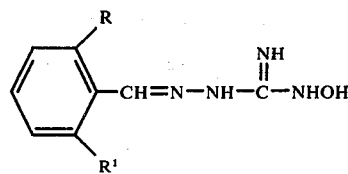

wherein R and $R^1$ are independently chlorine and fluorine, and the pharmacologically acceptable acid addition salts thereof.

The invention sought to be patented in its tenth subgeneric process aspect resides in the concept of a process for decreasing the psoriatic erythema experienced by a human being suffering from psoriasis which comprises administration of an effective amount of the compound of the formula:

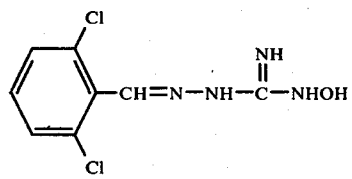

and the pharmacologically acceptable acid addition salts thereof.

The invention sought to be patented in its eleventh subgeneric process aspect resides in the concept of a process for decreasing the psoriatic erythema experienced by a human being suffering from psoriasis which comprises administration of an effective amount of the pharmacologically acceptable salt of the formula:

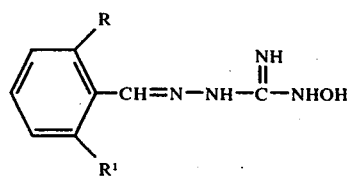

DESCRIPTION OF THE INVENTION

The present invention provides a process whereby a human being suffering from psoriasis is treated systemically for the disease with a compound of the formula:

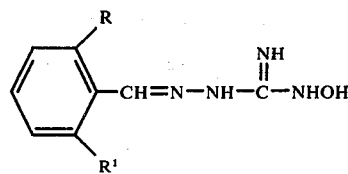

wherein R and $R^1$ are independently chlorine and fluorine, and the pharmacologically acceptable acid addition salts thereof.

For reasons of convenience, the hereinafter disclosed teaching of the practice of the process of the invention will be described by utilizing a specific embodiment of the invention. This specific embodiment is 1-(2,6-dichlorobenzylideneamino)-3-hydroxyguanidine. This limitation is made for convenience and clarity in describing the invention and is not meant to delimit the scope of the invention as herein disclosed and hereinafter claimed.

When used herein, the term "treating" means the systemic administration to a person suffering from psoriasis, of a compound of the formula:

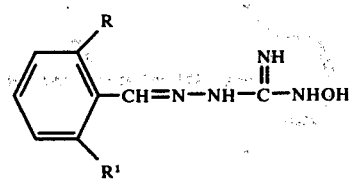

wherein R and R¹ are independently chlorine and fluorine and the pharmacologically acceptable acid addition salts thereof. As a result of the systemic administration of a compound or salt of the above formula a remission of the symptoms of the psoriatic patient, in most cases, will result. Thus, one affected by psoriasis can expect a decrease in scaling, erythema, size of the plaques, pruritis and other symptoms associated with psoriasis. The dosage of medicament and the length of time required for successfully treating each individual psoriatic patient may vary, but those skilled in the art of medicine will be able to recognize these variations and ajust the course of therapy accordingly.

The compounds of the process of the invention can be prepared and administered in a wide variety of oral and parenteral dosage forms.

For preparing compositions from the compounds described by this invention, inert, pharmacologically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet-disintegrating agents; it can also be an encapsulating material. In powders the carrier is finely divided solid which is in admixture with the finely divided compound. In the tablet the compound is mixed with carrier having the necessary binding properties in suitable proportions and compacted in the shape and size desired. The powders and tablets preferably contain from 5 or 10 to 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "preparation" is intended to include the formulation of the compound with encapsulating material as carrier providing a capsule in which the compound (with or without other carriers) is surrounded by carrier, which is thus in association with it. Similarly, cachets are included. Tablets, powders, cachets, capsules can be used for oral administration.

Liquid form preparations include solutions, suspensions and emulsions. As an example may be mentioned water-propylene glycol solutions for parenteral injection. Liquid preparations can also be formulated in solution in aqueous polyethylene glycol solutions. Aqueous suspensions suitable for oral use can be made by dispensing the finely divided compound in water with viscous material, natural or synthetic gums, resins, etc., for example, gum arabic, ion-exchange resins, methyl cellulose, sodium carboxymethyl cellulose and other well-known suspending agents.

Preferably, the pharmacological preparation is in unit dosage form. In such form, the preparation is subdivided in unit doses containing appropriate quantities of the compound, the unit dosage form can be a packaged preparation, the package containing discrete quantities of preparation, for example, packeted powders or vials or ampoules.

The unit dosage form can also be a capsule, cachet or tablet itself or it can be the appropriate number of any of these in packaged form. The quantity of compound in a unit dose of preparation may be varied or adjusted from 1 mg. to 100 mg. according to the particular application and the potency of the active ingredient.

In therapeutic use as agents for treating psoriasis, the compounds utilized in the process of this invention are administered at the initial dosage of about 0.02 mg. to 1.0 mg. per kilogram daily. The dosages, however, may be varied depending upon the requirements of the patient and the compound being employed. Generally, treatment is initiated with smaller dosages which are less than the optimum dose of the compound. Thereafter, the dosage is increased by small increments until optimum effect under the circumstances is reached. In general, the compounds of the invention are administered at a dosage level which will generally afford effective results without causing any harmful or deleterious side effects, and which is from about 0.02 mg. to about 1.0 mg. per kilogram per day. In particular, 1-(2,6-dichlorobenzylideneamino)-3-hydroxyguanidine may be employed in humans at a range from about 2 mg. to about 50 mg. per patient per day, although as aforementioned variations will occur. However, a dosage level that is in the range of from about 8 mg. to about 32 mg. per patient per day is most desirably employed in order to achieve effective results. For convenience, the total daily dosage may be divided and administered in portions during the day if desired.

When used herein, the term pharmacologically acceptable acid addition salt, means the salt obtained by reacting a benzylideneamino-3-hydroxyguanidine of the invention with a pharmacologically acceptable acid. Such acids will be familiar to those skilled in the art, e.g. acetic, hydrochloric, sulfuric, nitric, fumaric, and the like.

The subject matter which the applicant regards as his invention is particularly pointed out and distinctly claimed as follows:

1. A process for ameliorating the clinical manifestations of psoriasis in a human suffering from psoriasis which comprises administering to said human an effective amount of a compound of the formula:

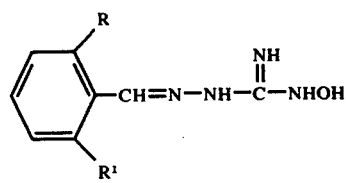

wherein R and R¹ are independently chlorine and fluorine, and the pharmacologically acceptable acid addition salts thereof.

2. The process of claim 1 wherein R and R¹ are chlorine.

3. The process of claim 2 wherein the pharmacologically acceptable acid is acetic.

4. The process of claim 2 wherein the pharmacologically acceptable acid is hydrochloric.

5. A process for decreasing the psoriatic scaling experienced by a human suffering from psoriasis which comprises administering to said human an effective amount of a compound of the formula:

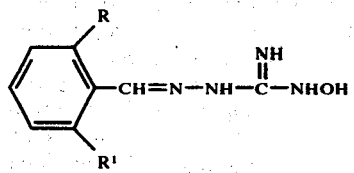

wherein R and $R^1$ are independently chlorine and fluorine, and the pharmacologically acceptable acid addition salts thereof.

6. The process of claim 5 wherein R and $R^1$ are chlorine.

7. The process of claim 6 wherein the pharmacologically acceptable acid is acetic.

8. The process of claim 6 wherein the pharmacologically acceptable acid is hydrochloric.

9. A process for decreasing the psoriatic erythema experienced by a human suffering from psoriasis which comprises administering to said human an effective amount of a compound of the formula:

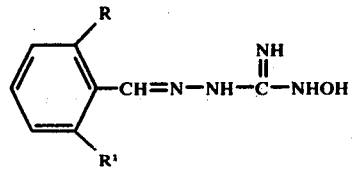

wherein R and $R^1$ are independently chlorine and fluorine, and the pharmacologically acceptable acid addition salts thereof.

10. The process of claim 9 wherein R and $R^1$ are chlorine.

11. The process of claim 10 wherein the pharmacologically acceptable acid is acetic.

12. The process of claim 10 wherein the pharmacologically acceptable acid is hydrochloric.

* * * * *